United States Patent [19]

Harada et al.

[11] Patent Number: 5,037,427

[45] Date of Patent: Aug. 6, 1991

[54] METHOD OF IMPLANTING A STENT WITHIN A TUBULAR ORGAN OF A LIVING BODY AND OF REMOVING SAME

[75] Inventors: Fumiaki Harada; Kyuta Sagae, both of Fuji; Masakiyo Nobuyoshi, Kitakyushu, all of Japan

[73] Assignee: Terumo Kabushiki Kaisha, Tokyo, Japan

[21] Appl. No.: 607,767

[22] Filed: Oct. 30, 1990

Related U.S. Application Data

[62] Division of Ser. No. 440,513, Nov. 22, 1989, abandoned.

[30] Foreign Application Priority Data

Mar. 25, 1987 [JP] Japan .................................. 62-70781

[51] Int. Cl.⁵ .............................................. A61B 17/00
[52] U.S. Cl. .................................... 606/108; 606/194; 604/96; 623/1
[58] Field of Search ............................... 604/104–109, 604/96; 606/192, 194, 108; 623/1, 12

[56] References Cited

U.S. PATENT DOCUMENTS

| | | | |
|---|---|---|---|
| 3,868,956 | 3/1975 | Alfidi et al. | 606/194 |
| 4,332,254 | 6/1982 | Lundquist | 606/194 |
| 4,503,569 | 3/1985 | Dotter | 606/200 X |
| 4,665,906 | 5/1987 | Jervis | 606/78 |
| 4,762,128 | 8/1988 | Rosenbluth | 606/192 |
| 4,795,458 | 1/1989 | Regan | 606/194 X |
| 4,969,890 | 11/1990 | Sugita et al. | 623/1 X |

FOREIGN PATENT DOCUMENTS 57-89859  6/1982  Japan .

OTHER PUBLICATIONS

Encyclopedia of Chemical Technology, 3rd Ed., vol. 20, 1982 (John Wiley and Sons; New York, N.Y.), "Shape-Memory Alloys", (pp. 726-736).
Titanium-Zirconium, vol. 30, No. 4, Oct. 1982; "Shape Memory and Super-Elasticity Effects in NiTi Alloys", by Y. Suzuki; pp. 185-192.

Primary Examiner—C. Fred Rosenbaum
Assistant Examiner—Corrine Maglione
Attorney, Agent, or Firm—Frishauf, Holtz, Goodman & Woodward

[57] ABSTRACT

Disclosed are an instrument for expanding a tubular organ such as a blood vessel and for keeping the tubular organ expanded for a predetermined period of time, and a catheter for mounting said instrument at a desired position within the tubular organ, said catheter being capable of moving and recovering the instrument mounted within the tubular organ. The instrument is formed of a two-way shape memory alloy and expands or shrinks in the radial direction, in accordance with changes in temperature. At least one side hole is formed at the distal end portion of the catheter, on which the instrument is detachably mounted.

6 Claims, 2 Drawing Sheets

F I G. 1(a)    F I G. 1(b)
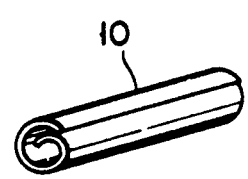
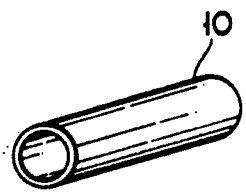
F I G. 2(a)    F I G. 2(b)
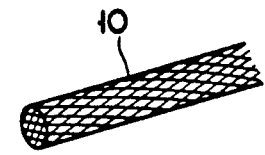
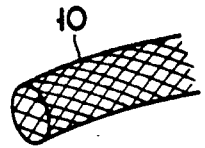
F I G. 3(a)    F I G. 3(b)
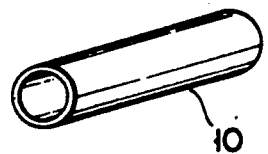
F I G. 4(a)    F I G. 4(b)
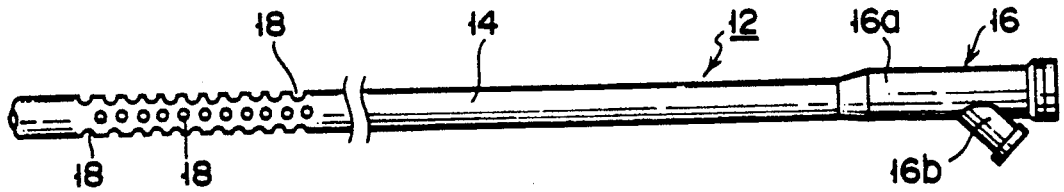
F I G. 5

METHOD OF IMPLANTING A STENT WITHIN A TUBULAR ORGAN OF A LIVING BODY AND OF REMOVING SAME

This application is a division of application Ser. No. 07/440,513, filed Nov. 22, 1989, now abandoned, which is a continuation of International Application No. PCT/JP88/00306, filed Mar. 25, 1988.

TECHNICAL FIELD

The present invention relates to an expansion retainer for ensuring a desired inner diameter of a tubular organ and to a catheter for introducing or recovering the expansion retainer.

PRIOR ART

Where a narrowed portion of, for example, the coronary arteries is expanded with an angioplasty catheter, it is necessary to take measures for preventing the expanded portion from being narrowed again. In such a case, an expansion retainer, hereinafter referred to as "stent", is generally used for ensuring a desired inner diameter of a tubular organ.

A stent prepared by weaving a stainless steel wire in the form of a net is proposed in "Surgery, 1986, Vol. 99, No. 2, pp. 199-205". Another stent formed of a one-way shape memory alloy is proposed in Published Examined Japanese Patent Application No. 61-6655. For ensuring expansion of, for example, a blood vessel by using a stent formed of stainless steel, the stent is introduced into a predetermined position of the blood vessel through an angioplasty catheter Then, a balloon disposed at the distal end portion of the catheter is expanded so as to expand the stent to have a diameter conforming with the inner diameter of the blood vessel. In the case of using a stent formed of a one-way shape memory alloy, the stent introduced into a predetermined position of a blood vessel is heated by, for example, warm water so as to expand the stent.

The stent once expanded cannot be deformed unless an external force is applied thereto. Thus, it is impossible to take out the stent left in the blood vessel even after recovery of the body part to which the surgical operation was applied. Naturally, it is of high importance for the stent to be compatible with a living body. What should also be noted with respect to the prior art is that, even if the stent is found to have been left in an erroneous position, it is very difficult to change the position of the stent once expanded.

The present invention, which has been achieved in view of the situation described above, is intended to provide a stent for a tubular organ, which can be freely brought back to the small original shape even after expanded within a tubular organ, thus making it possible to recover the stent once introduced into the tubular organ, and to change freely the position of the stent once expanded within the tubular organ, and to provide a catheter for operating the stent.

DISCLOSURE OF THE INVENTION

To solve the above-noted problems inherent in the prior art, a stent of the present invention is formed of a two-way shape memory alloy. Also, the stent is mounted at the distal end of a catheter having a side hole. Cooling water supplied through the side hole is brought into contact with the stent, as desired, so as to control the shrinkage and expansion of the stent, as desired.

According to one embodiment of the present invention, there is provided a stent for a tubular organ, characterized in that the stent consists of a substantially cylindrical shaped body formed of a two-way shape memory alloy capable of expansion or shrinkage in the radial direction in accordance with changes in temperature.

It is desirable for the cylindrical body of the two-way shape memory alloy to be in the expanded state about the body temperature and in the shrunk state at a temperature substantially lower the body temperature.

According to another embodiment of the present invention, there is provided a catheter equipped with a stent for a tubular organ, characterized by comprising a catheter tube open at the proximal end or both proximal and distal ends, at least one side hole, which communicates with said opening, being formed at the circumferential surface near the distal end of said catheter tube; a hub portion mounted to communicate with the distal end of the catheter tube; and a stent for ensuring a desired inner diameter of a tubular organ, said stent consisting of a cylindrical body formed of a two-way shape memory alloy, being capable of expansion or shrinkage in the radial direction in accordance with changes in temperature, and being mounted to cover at least a part of the distal end portion of the catheter tube including the side hole.

It is desirable for the hub portion to be formed of a branched hub having two ports, with a hemostatic valve being mounted to one of said ports.

The shape memory alloy used in the present invention has a transformation temperature above which the alloy is deformed into a shape memorized in advance. In the two-way shape memory alloy, the alloy can be freely deformed for the memory purpose at a temperature lower than the transformation temperature. The shape thus memorized is exhibited at a temperature higher than the transformation temperature. It should be noted that the alloy continues to keep its shape even after the temperature is lowered below the transformation temperature. On the other hand, the two-way shape memory alloy used in the present invention also permits memorizing the shape at a temperature lower than the transformation temperature with the result that two different shapes can be reversibly exhibited with a boundary set by the transformation temperature. The term "substantially cylindrical shaped body" used in the present specification should be interpreted to include, for example, a cylindrical body having a spiral cross section and a coil-shaped cylindrical body as well as the ordinary cylindrical body.

BRIEF DESCRIPTION OF THE DRAWINGS

FIGS. 1(a) and 1(b) are side views each showing a stent for a tubular organ according to one embodiment of the present invention;

FIGS. 2(a), 2(b), 3(a), 3(b), 4(a) and 4(b) are oblique views showing stents according to other embodiments of the present invention, (a) and (b) showing shrunk and expanded states, respectively;

FIG. 5 is a side view showing a catheter used for operating a stent of the present invention;

BEST MODE FOR CARRYING OUT THE INVENTION

FIGS. 1(a) and 1(b) collectively show a stent 10 for a tubular organ according to one embodiment of the present invention. The stent 10, which is formed by spirally winding a flat wire of a bidirectional shape memory alloy such as Ni-Ti binary alloy, Cu-Al-Ni ternary alloy or Cu-Zn-Al ternary alloy, keeps a shape expanded in the radial direction as shown in FIG. 1(b) at temperatures about the body temperature, i.e., at about 35 to 37° C., and keeps a shape shrunk in the radial direction as shown in FIG. 1(a) at temperatures substantially lower than the body temperature, i.e., at about 15 to 20° C. Where the flat wire is 0.04 mm in thickness and 1 mm in width and consists of a Ni-Ti binary alloy two-way shape memory alloy containing essentially about 51 atomic % of Ni and the balance substantially Ti, the stent 10, which is about 2 mm in inner diameter at the body temperature, can be shrunk to have an inner diameter of about 1.4 mm at 15° C or lower. The inner diameter, length, etc. of the stent 10 can be determined appropriately to conform with the inner size of the tubular organ within which the stent 10 is mounted. In short, the stent under an expanded state should have an outer diameter substantially conforming with the inner diameter of a tubular organ such as a blood vessel, and the stent under a shrunk state should have an outer diameter small enough to permit the stent to be introduced into the desired position within the tubular organ.

The shape of the stent 10 is not restricted to a spiral shape shown in FIG. 1, as far as the stent is substantially cylindrical. For example, the stent may have a spiral cross section as shown in FIG. 2(a) under a shrunk state and is cylindrical as shown in FIG. 2(b) under an expanded state. Also, a net of a two-way shape memory alloy wire may be formed into a cylindrical body as shown in FIG. 3. In this case, the mesh of the net is expanded from the shrunk state shown in FIG. 3(a) into the expanded state shown in FIG. 3(b) when the stent 10 is expanded in the radial direction. Further, the stent 10 may consist of a pipe as shown in FIG. 4. Naturally, the pipe under a shrunk state shown in FIG. 4(a) is expanded as shown in FIG. 4(b) depending on the temperature.

Figure 6:
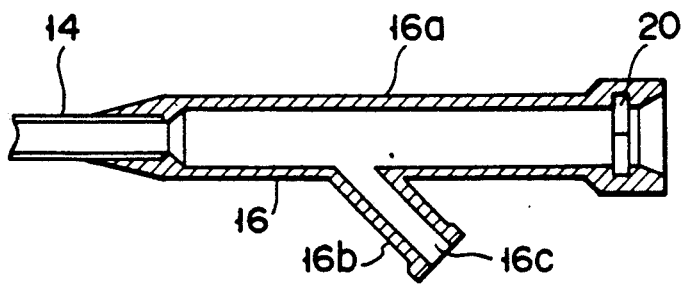
FIG. 6 is a cross sectional view showing in a magnified fashion the hub portion of the catheter shown in FIG. 5.

A catheter 12 shown in FIG. 5 is used for introducing the stent 10 into a desired position within a tubular organ of a living body. The catheter 12 comprises a catheter tube 14 open at both ends and a hub portion 16 mounted at the proximal end of the catheter tube 14 in a manner to communicate with the inner space of the catheter tube. The catheter tube 14 is formed of, for example, ethylene-vinyl acetate copolymer. On the other hand, the hub portion 16 is formed of, for example, polycarbonate. A number of side holes 18 are formed through the wall near the distal end of the catheter tube 14 such that a cooling liquid introduced into the catheter tube 14 is discharged radially through these side holes. The hub portion 16 comprises a linear cylindrical portion 16a through which a guide wire is introduced into the catheter tube 14, and a branched portion 16b branched at the central portion of the linear cylindrical portion 16a, as shown in FIG. 6. A hemostatic valve 20 formed of a soft material such as a silicone rubber is mounted at the proximal end of the linear cylindrical portion 16a so as to prevent the leakage of, for example, blood. A cooling liquid or the like is introduced through a port 16c of the branched portion 16b.

Figure 7:
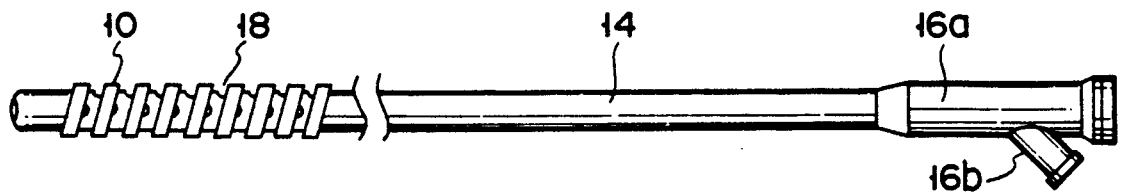
FIG. 7 is a side view showing how the stent shown in FIG. 1 is mounted to the catheter shown in FIG. 5.

In introducing the stent 10 into a desired portion within a tubular organ, the stent 10 is mounted first at the distal end portion of the catheter tube 14 in a manner to cover the side holes 18. Then, a cooling liquid, e.g., an ice-cooled physiologic saline, is introduced through the port 16c and discharged through the side holes 18 so as to cool the stent 10 to 15 to 20° C. As a result, the stent 10 is shrunk so as to be brought into direct contact with the wall of the catheter tube 14 at the portion of the side holes 18, as shown in FIG. 7.

Figure 8:
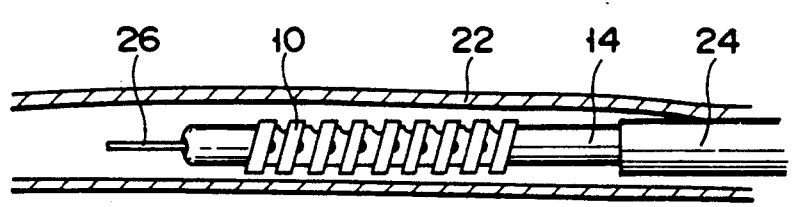
FIGS. 8 and 9 are cross sectional views showing how the catheter shown in FIG. 7 is operated for leaving a stent mounted within a tubular organ.
Figure 9:
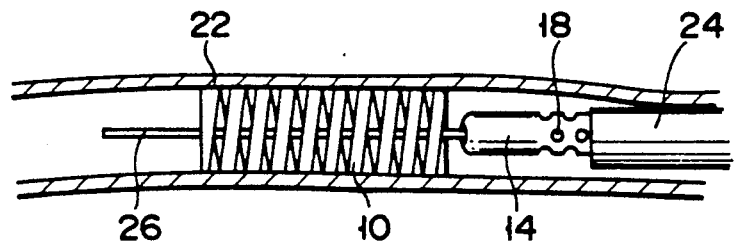

In the next step, the catheter tube 14 is introduced into a desired position within a tubular organ 22 through a guide catheter 24 introduced in advance into the tubular organ 22, as shown in FIG. 8. In this step, the ice-cooled physiologic saline is kept flowing out of the side holes 18. Also, a guide wire 26 is used for the introduction of the catheter tube 14 into the tubular organ 22. When the stent 10 mounted at the distal end portion of the catheter tube 14 has arrived at the desired position within the tubular organ 22, supply of the ice-cooled physiologic saline is stopped. As a result, the stent 10 is gradually warmed by the heat of the living body. When warmed to a temperature near the body temperature, the stent 10 is expanded to be directly contacted with the inner wall of the tubular organ 22, as shown in FIG. 9. Under this condition, the distal end portion of the catheter tube 14 can be easily withdrawn, with the expanded stent 10 left at the desired position within the tubular organ 22.

Where the stent 10 is recovered from within the tubular organ 22, the distal end portion of the catheter tube 14 is inserted into the stent 10, and an ice-cooled physiologic saline introduced through the port 16c is discharged through the side holes 18 formed at the distal end portion of the catheter tube 14. As a result, the stent 10 is cooled and shrunk to be directly contacted with the distal end portion of the catheter tube 14 as shown in FIG. 7. Naturally, the stent 10 can be recovered by pulling out the catheter tube 14. Similarly, the mounting position of the stent 10 within the tubular organ can be easily changed in the present invention.

It is possible to determine appropriately the number of side holes 18 formed at the distal end portion of the catheter tube 14 as well as the hole-forming region in view of the size of the stent, etc.

As described above in detail, the stent of the present invention is in the form of a cylindrical body of a two-way shape memory alloy which is expanded or shrunk depending on changes in temperature of the alloy on the basis of the normal body temperature. The particular construction of the invention produces prominent effects. For example, it is possible to recover the stent once expanded within a tubular organ. It is also possible to change the mounting position of the stent once mounted within a tubular organ. Further, the catheter of the present invention for operating the stent comprises side holes formed at the distal end portion. Naturally, the expanded stent mounted at the distal end portion of the catheter can be cooled by a cooling liquid discharged through the side holes so as to shrink the stent. It follows that the catheter makes it possible to introduce and recover the stent without difficulty.

INDUSTRIAL APPLICATION

The instrument of the present invention for ensuring the inner diameter and the catheter equipped with the instrument are inserted into a tubular organ such as a blood vessel of the human being or animals so as to keep the tubular organ expanded to have a desired inner diameter for at least a predetermined period.

We claim:

1. A method of implanting a stent within a tubular organ of a living body and removing the stent from the tubular organ, which comprises the steps of:

mounting a cylindrical shaped stent made of a two-shape memory allow on a distal end portion of a catheter tube having at least one hole in said end portion, said stent being capable of expanding or shrinking in the radial direction thereof if accordance with changes in temperature;

introducing a cooling liquid into said distal end portion of the catheter tube thereby to discharge the cooling liquid through said hole, and to shrink the stent so as to bringing the stent in contact with the outer wall of said distal end portion of the catheter tube;

introducing said distal end portion of the catheter tube into a desired portion of said tubular organ through a guide catheter introduced in advance, while keeping the cooling liquid flowing out of said hole;

discontinuing the supply of the cooling liquid thereby warming the stent through a heat from the living body thereby expanding the stent so as to bringing the stent in contact with the inner wall of the tubular organ;

withdrawing the distal end portion of the catheter tube from the tubular organ, leaving the stent as it is thereby implanting the stent at said desired portion of said tubular organ;

introducing said distal end portion of the catheter tube into the stent implanted in said desired portion of said tubular organ;

introducing a cooling liquid into said distal end portion of the catheter tube thereby to discharge the cooling liquid through said hole, and to shrink the stent so as to bring the stent in contact with the outer wall of said distal end portion of the catheter tube; and withdrawing the distal end portion of the catheter tube from the tubular organ with the stent being mounted on the distal end portion of the catheter tube, thereby removing the stent from the tubular organ.

2. The method according to claim 1, wherein said cylindrical body is in the form of a hollow coil.

3. The method according to claim 1, wherein said cylindrical body is of a spiral cylindrical shape.

4. The method according to claim 1, wherein said cylindrical body is in the form of a pipe.

5. The method according to claim 1, wherein said cylindrical body has a mesh structure.

6. The method according to claim 1, wherein said two-way shape memory alloy is selected from the group consisting of alloys of Ni-Ti binary alloy, Cu-Al-Ni ternary allow and Cu-Zn-Al ternary alloy.

* * * * *